United States Patent [19]

Remington et al.

[11] 4,361,647

[45] Nov. 30, 1982

[54] SANDWICH IMMUNOASSAY AND COMPOSITIONS FOR USE THEREIN

[75] Inventors: Jack S. Remington; Fausto G. Araujo, both of Palo Alto, Calif.

[73] Assignee: Palo Alto Medical Research Foundation, Palo Alto, Calif.

[21] Appl. No.: 152,328

[22] Filed: May 22, 1980

[51] Int. Cl.³ .............................................. C12Q 1/66
[52] U.S. Cl. .................................... 435/7; 23/230 B; 424/8; 424/12
[58] Field of Search .............. 435/7; 23/230 B; 424/8, 424/12

[56] References Cited

U.S. PATENT DOCUMENTS 4,200,436  4/1980  Mochida et al. .................. 23/230 B
4,235,869  11/1980  Schwarzberg .......................... 424/8

FOREIGN PATENT DOCUMENTS 8473  3/1980  European Pat. Off. .

OTHER PUBLICATIONS

Noel R. Rose et al., Editors, Principles of Immunology, Second Edition, MacMillan Publishing Co., pp. 49–52, and 513–528.

Primary Examiner—Robert J. Warden
Attorney, Agent, or Firm—Julian Caplan

[57] ABSTRACT

An improved sandwich immunoassay for *Toxoplasma gondii* antigens associated with acute forms of Toxoplasma infection is disclosed. The assay employs either an F(ab')$_2$ fragment of IgG which reacts specifically with such antigens or a monoclonal antibody for such antigens as the substrate layer in the sandwich. The assay is sensitive and, unlike prior sandwich assays for the antigen, is not affected significantly by cross-reactions with rheumatoid factor.

6 Claims, No Drawings

SANDWICH IMMUNOASSAY AND COMPOSITIONS FOR USE THEREIN

REFERENCE TO GOVERNMENT GRANTS

The government has rights in this invention pursuant to grant AI04717 awarded by the National Institutes of Health.

DESCRIPTION

1. Technical Field

The invention concerns sandwich immunoassays, especially one for detecting *Toxoplasma gondii* antigen in body fluids, and compositions useful in such immunoassays.

2. Background Art

Sandwich immunoassays involve a technique in which an antigen layer is interposed or "sandwiched" between an unlabeled antibody substrate layer and a labeled antibody overlayer. Sandwich tests have been commonly used as a diagnostic tool to detect the presence of antigens in body fluids. In assaying a sample of body fluid for a given antigen, an antibody for the antigen is adsorbed on a solid surface and the test sample of body fluid is applied to the adsorbed layer of antibody. After a suitable incubation period the surface is washed to remove nonadsorbed entities from any adsorbed antibody-antigen complexes. A labeled antibody for the antigen is then applied to the surface. After incubation the surface is washed again to remove nonadsorbed entities. The presence of labeled antibody (in the form of an adsorbed antibody-antigen-labeled antibody complex) on the surface is then determined by appropriate means depending on the type of label used. A positive determination indicates antigen was present in the test sample of fluid; a negative determination indicates it is not present. The determination may be quantitative by comparing its intensity with an intensity curve derived from assaying samples of known antigen concentration. The "sensitivity" of the test relates to the ability of the test to detect antigen in a fluid that indeed contains the antigen. If the sensitivity of the test is poor, it will give significant false-negative results. The "specificity" of the test concerns the extent to which the antibody enters into cross-reactions with antigens other than the antigen to which the assay is directed. If such cross-reactions occur, the test may give a false-positive result, thus leading to an erroneous diagnosis.

The discovery of the presence of circulating *Toxoplasma gondii* antigens in sera of infected animals was recently reported by Raizman, R. E., and Neva, F. A., Detection of circulating antigen in acute experimental infections with *Toxoplasma gondii, J Infect Dis*, 132:44-48, 1975. That report suggests the possibility of using a sandwich immunoassay for detecting Toxoplasma antigenemia. In this regard the currently used immunoassays for Toxoplasma, the Sabin-Feldman and indirect fluorescent antibody tests, detect Toxoplasma antibodies rather than Toxoplasma antigens in sera. However, the use of a sandwich immunoassay for circulating Toxoplasma antigens in the sera of individuals suspected of having acute Toxoplasmosis has been reported by van Knapen, F., and Panggabean, S. O., Detection of circulating antigen during acute infections with *Toxoplasma gondii* by enzyme-linked immunosorbent assay, *J Clin Microbiol*, 6:545-47, 1977. They used IgG containing Toxoplasma antibodies and enzyme-labeled Toxoplasma antibody and reported detecting circulating Toxoplasma antigens in 64 of 1,116 serum samples. The accuracy of the assays as regards the actual presence or absence of acute or latent infection in the individuals was not reported.

The present applicants also ran sandwich immunoassays for Toxoplasma antigenemia using IgG containing Toxoplasma antibodies and serum samples of individuals whose state of Toxoplasmosis was known. As described in detail below, applicants found these assays produced a significant percentage of false-positive results due to cross-reaction of the antibodies with rheumatoid factor.

A prime object of the present invention is to provide the means and technique for carrying out a sandwich immunoassay of body fluids for antigens, particularly those antigens which would be of diagnostic usefulness in patients with acute infections with *Toxoplasma gondii*.

DISCLOSURE OF INVENTION

One aspect of the invention is an improvement in a sandwich immunoassay for detecting an antigen in a test sample of animal (humans and lower organisms of the Animalia kingdom) body fluid. The immunoassay includes the following steps:

(a) adsorbing an antibody for the antigen onto a solid surface;

(b) applying the test sample to the adsorbed antibody and incubating the resulting mixture;

(c) separating the adsorbed fraction from the nonadsorbed fraction of the incubated mixture of step (b);

(d) applying a labeled antibody for the antigen to the adsorbed fraction of step (e) and incubating the resulting mixture;

(e) separating the adsorbed fraction from the nonadsorbed fraction of the mixture of step (d); and (f) determining the presence of said labeled antibody in the adsorbed fraction of step (e).

The improvement lies in using an F(ab')$_2$ fragment of IgG antibody for the antigen as the antibody of step (a).

Another aspect of the invention is an improvement in an embodiment of the above described sandwich immunoassay that is used to detect *Toxoplasma gondii* antigens in the body fluids of animals. In this aspect of the invention either an F(ab')$_2$ fragment of IgG containing *Toxoplasma gondii* antibody or a monoclonal antibody for antigens of *Toxoplasma gondii* is used as the antibody of step (a) and a labeled *Toxoplasma gondii* antibody is used as the labeled antibody of step (d).

A third aspect of the invention is a composition for use in a sandwich immunoassay for detecting an antigen. The composition comprises an F(ab')$_2$ fragment of IgG containing an antibody for the antigen adsorbed on a solid surface.

DETAILED DESCRIPTION OF EMBODIMENTS OF THE INVENTION

The antigens that may be detected in the improved sandwich immunoassay of the invention include foreign bodies such as drugs, hormones, and complex macromolecular substances such as proteins that cause the formation of antibodies that are contained in the F(ab')$_2$ fragment of IgG. Specific examples of circulating antigen that may be detected by the assay are the *Toxoplasma gondii* antigens associated with the acute forms of Toxoplasma infection, *Hemophilus influenzae, Neisseria meningitidis, staphylococcus,* Trypanosomes, Shistosomes, *malaria pneumococci, pseudomonas,* and other gram negative rod bacteria.

When the assay is used to diagnose an infection, disease, or other condition known to be associated with a given organism, the test sample of body fluid used in the assay should be one that would typically contain the antigen if the infection, disease or condition exists. For instance, Toxoplasma affects mammals such as cattle, sheep, pigs, humans, rabbits, rats, dogs, and cats and avians such as chickens and ducks. *Toxoplasma gondii* antigens may be present in many of the body fluids of such infected animals including the serum, peritoneal fluid, urine, saliva, vaginal fluid, cerebrospinal fluid, and amniotic fluid.

In the first step of the immunoassay for *Toxoplasma gondii* a layer of either an F(ab')$_2$ fragment of IgG which reacts specifically with antigens of *Toxoplasma gondii* or a monoclonal IgG antibody for antigens of *Toxoplasma gondii* is adsorbed onto a solid surface. Microtiter plates that are well known and available may be used to provide the solid surface onto which the layer is adsorbed. These plates have a plurality of wells or depressions into which the antibodies are placed and are typically made from materials that are chemically inert to the reagents used in immunoassays. Such materials include polystyrene, polyolefins such as polyethylene and polypropylene, chlorinated polyolefins such as polyvinylchloride, polyesters such as polyethyleneterephthalate, polyamides, and polyurethanes. The F(ab')$_2$ fragment may be prepared by known methods. A donor animal is immunized against *Toxoplasma gondii* and serum is taken from the animal. IgG is fractionated from the serum by known chemical or physical means, such as by treating the serum with precipitating agents such as alcohols, ammonium sulfate, or fatty acids or by subjecting it to column chromatography. The F(ab')$_2$ fragment is made by cleaving the IgG with pepsin using known procedures. When the immunoassay is used to detect another antigen, an F(ab')$_2$ fragment containing antibodies for the other antigen may be made in a similar manner.

The monoclonal IgG antibodies used in the *Toxoplasma gondii* assay may also be made by conventional procedures. Briefly, myeloma cells are fused with spleen cells taken from a donor animal immunized against the antigen to form hybridomas. The hybridomas are cultured in growth media and the supernatants from the cultures are withdrawn and tested for antibody for the antigen. IgG is extracted by gel filtration from the supernatants that test positive. The extracts may be characterized as regards their activity against membrane and/or cytoplasmic antigens by radioimmunoassay.

The protein concentration of the antibody preparation applied to the solid surface in the first step of the assay may affect the ability of the antibody preparation to coat the surface with an adsorbed layer of antibody. In the case of an F(ab')$_2$ fragment containing *Toxoplasma gondii* antibodies the optimum concentration was found to be in the range of 20 to 40 mcg/ml. If necessary the antibody preparation may be diluted with standard buffer solutions to provide such optimum concentrations. The antibody preparation should be applied to the surface under conditions that optimize the adsorption of the antibodies to the surface. Usually the application will be done at 3° to 6° C. and the preparation will be left in contact with the surface for 18 to 24 hr before draining excess antibody preparation from the surface. After the excess is drained off, it is desirable to wash the surface with saline to clear the surface of any nonadsorbed entities.

The sample of body fluid is applied to the adsorbed layer of antibody and left in contact therewith to incubate in the second step of the assay. The sample may be freshly acquired or taken from storage. If the sample is stored, it should be maintained under conditions that preserve the antigen's reactivity. Typically, body fluids may be frozen and kept for prolonged periods at temperatures below about −20° C. without losing their reactivity. The conditions (time and temperature) under which the sample is incubated in contact with the adsorbed antibody are desirably those that optimize the likelihood of stable binding between the antibody and the antigen to which the assay is directed. In the *Toxoplasma gondii* assay incubation at 37° C. for about 2 hr was found to be optimum.

After incubation, that portion of the sample which has not bound to the adhered antibody is drained from the surface and the surface is washed with saline to clear it of any additional nonadsorbed entities. Following the wash, a labeled antibody for the antigen is applied to the surface and allowed to incubate. Such labels include radioactive labels such as iodine isotopes, fluorescent labels such as fluorescein isothiocyanate, and enzyme labels such as peroxidases or phosphatases. Techniques for conjugating such labels and antibodies are known. For the *Toxoplasma gondii* assay enzyme labels are preferred because of their high degree of sensitivity. The same incubation conditions as were used to incubate the sample and adsorbed unlabelled antibody may be used. Following the incubation the labeled antibody is drained off and the surface is again washed with saline to eliminate nonadsorbed materials.

The last step in the assay is reading the surface for the presence of labeled antibody. If it is present, it will be so substantially in the form of an antibody-antigen-labeled antibody complex. The reading technique used will depend upon the nature of the label involved, eg, by a scintillation counter for radioactive labels, by fluorometry for fluorescent labels and by spectrophotometry or visual observation for enzyme labels. If an enzyme label is used the last step may involve the substep of applying a substrate to the surface that reacts with the enzyme to produce a characteristic spectrophotometric effect.

The following examples further illustrate the various aspects of the invention. These examples are not intended to limit the invention in any manner.

EXAMPLE 1

This example illustrates the use of F(ab')$_2$ fragments of IgG containing *Toxoplasma gondii* antibodies in a sandwich immunoassay as compared to previously used methods.

Sera Collection

Twenty-three samples of serum were from 22 patients in whom acute infection with *Toxoplasma gondii* was diagnosed. The sera were obtained 1 to 20 weeks after clinical onset of the disease. The diagnosis of acute infection was based on clinical findings, lymph node biopsy and serologic test results. Fifty-five samples were from 55 children and adults in whom infection with *Toxoplasma gondii* had occurred at least 2 years before the serum sample was obtained (chronic infection). The diagnosis of the acute infection in these 55 individuals had been made by the criteria stated above. Twenty-eight samples were from 28 individuals who had no serologic or clinical evidence of infection with *Toxoplasma gondii;* their sera were negative (<1:4) in the Sabin-Feldman dye test (DT) and negative (<1:10) in the IgM-fluorescent antibody (IgM-IFA) test. Thirteen samples were from 13 individuals whose sera were negative in the DT and IgM-IFA tests but positive for rheumatoid factor (RF). The RF titers in these sera ranged from 1:160 to 1:2560, as determined by the latex agglutination method (RAPi/TEX RF kit; Behring Diagnostics, American Hoechst Corp, Somerville N.J.).

Most serum samples were collected 3 to 4 days prior to assay and were kept refrigerated at 4° C. until used. Serum samples from some of the acutely infected patients had been collected at the time of diagnosis of acute infection and had been kept frozen at −90° C. in tightly sealed vials for 1 month to 4 years prior to use.

Preparation of antibodies to Toxoplasma

Sera were collected from one normal, DT negative rabbit and from three rabbits that had been initially infected with the C56 strain and then challenged with the RH strain of *Toxoplasma gondii* one month later. The rabbits were bled one month after the challenge; the DT titers ranged from 1:16,000 to 1:256,000. These sera were pooled, and the gamma globulin fraction was separated by ammonium sulfate precipitation. IgG was then isolated from this fraction by chromatography. The DT titers in the purified IgG preparations ranged from 1:16,000 to 1:64,000.

The F(ab')$_2$ fragment of IgG was prepared by digesting IgG from normal rabbits (NIgG) or IgG from Toxoplasma-infected rabbits (TIgG) (described above) with pepsin.

Preparation of Toxoplasma Antigen

Toxoplasma antigen was prepared using *Toxoplasma gondii* trophozoites from the peritoneal exudate of mice infected 3 days earlier with the RH strain of the parasite. Upon removel, the exudate was immediately placed into tubes kept in an ice bath. After centrifugation at 1000×g for 10 min, the sediment containing cells and parasites were resuspended in cold phosphate buffered saline, pH 7.2 (PBS), washed three times with PBS, and filtered. The parasites were then disrupted in the cold, using a Biosonik IV sonicator (Bronwill Scientific, Rochester, N.Y.) set at 60 cycles for 30 seconds. The sonicate was centrifuged at 1000×g for 20 min and then recentrifuged at 10,000×g for 30 min. The presence of Toxoplasma antigens in this lysate was demonstrated by double diffusion in agar (DDA) and by counterimmunoelectrophoresis (CIE) using 1% agarose gel (Sigma Chemical Co, St Louis, Mo.) in 0.05 M barbital buffer, pH 8.2. The protein concentration of the final lysate preparation was 0.5 mg/ml. It was diluted in normal human serum and used as a positive control each time the sandwich immunoassay was performed.

Preparation of Enzyme-Labeled Antibody

Alkaline phosphatase (EC 3.1.3.1) type VII from calf intestine (Sigma Chemical Co, St Louis, Mo.) was coupled to the purified IgG from rabbits infected with *Toxoplasma gondii* (described above) using the one step glutaraldehyde method described by Engvall and Pearlman, *J Immunol*, 109:129–35, 1972.

Performance of Sandwich Immunoassay for Toxoplasma Antigen

Polyvinyl chloride and polystyrene plates were divided into three sections, each consisting of four rows containing eight wells in each row. The wells of a given section were coated with NIgG, the F(ab')$_2$ fragment of NIgG, TIgG, or the F(ab')$_2$ fragment of TIgG. The protein concentration of each of the antiserums was 300 μg/ml in 0.1 M carbonate buffer, pH 9.8. For the coating procedure, 0.1 ml of a preparation was added to the appropriate wells and the plates incubated at 4° C. for 18 hr. Just prior to adding the serum samples, the wells were drained and washed three times with saline containing 0.5% polyoxyethylene sorbitan monolaurate (available under the designation Tween 20). One-tenth milliliter of each serum sample to be tested for presence of antigen was added to the wells, and the plates were covered and incubated at 37° C. for 2 hr. After incubation, the serum in the wells was poured off and the wells were washed three times with saline-Tween 20. Thereafter, 0.1 ml of the appropriate dilution of the enzyme-labeled IgG prepared in PBS containing 4% bovine serum albumin (BSA) and 0.05% Tween 20, pH 7.4, was added to the wells, and the plates were incubated at 37° C. for 60 min. The wells were washed three times with saline-Tween 20, and then 0.1 ml of an enzyme substrate was added to the wells. The substrate was p-nitrophenyl phosphate disodium (Sigma Chemical Co, St Louis, Mo.) dissolved to effect a final concentration of 0.1% in 0.05 M carbonate buffer containing 0.001 M MgCl$_2$. After 30 to 60 min at room temperature, the reaction was stopped by adding one drop of a 3 M NaOH solution to each well. The results were evaluated visually and by spectrophotometer at 405 nm. A yellow color developed in the wells in which a chemical change in the enzyme substrate had occurred.

The controls used in the test were: (1) a positive control serum prepared by mixing 50 μg of Toxoplasma antigen with 1 ml of normal human serum that was negative in the DT and IgM-IFA test and negative for RF; this control was used in dilutions from 1:10 to 1:2048; (2) a negative control serum that yielded negative results on initial and repeat testing; (3) a conjugate control in which saline substituted for the serum; and (4) a substrate control in which saline substituted for both the serum and the conjugate.

Reproducibility and Sensitivity

The reproducibility of results obtained when Toxoplasma antigen described above was employed in the sandwich immunoassay to detect Toxoplasma antigen is shown in Table 1. In Table 1, "OD" means the mean optical density, "V" means visual, "N" means negative, and "P" means positive. When evaluated by spectrophotometer, there was excellent agreement in results obtained with the same antigen preparation on seven different days. When read by visual observation, a positive result correlated with an optical density of 0.01. In testing the sensitivity of the test, both spectrophotometer and visual readings regularly detected from 31.25 to 62.5 ng of protein per ml.

TABLE 1

| Protein in Toxoplasma antigen preparation (nanograms/ml) | Readings with | | | | | |
|---|---|---|---|---|---|---|
| | NIgG | | TIgG | | F(ab')$_2$ fragment of TIgG | |
| | OD | V | OD | V | OD | V |
| 500 | .00 | N | .38 ± .006 | P | .54 ± .018 | P |
| 250 | .00 | N | .19 ± .0075 | P | .27 ± .0075 | P |
| 125 | .00 | N | .10 ± .037 | P | .10 ± .0075 | P |
| 62.5 | .00 | N | .07 ± .026 | P | .06 ± .003 | P |
| 31.25 | .00 | N | .02 ± .0075 | P | .02 ± .003 | P |
| 15.5 | .00 | N | .00 | N | .00 | N |
| Negative Control | .00 | N | .00 | N | .00 | N |
| Conjugate Control | .00 | N | .00 | N | .00 | N |

TABLE 1-continued

| Protein in Toxo-plasma antigen preparation (nanograms/ml) | Readings with | | | | | |
|---|---|---|---|---|---|---|
| | NIgG | | TIgG | | F(ab')2 fragment of TIgG | |
| | OD | V | OD | V | OD | V |
| Substrate Control | .00 | N | .00 | N | .00 | N |

Results in Sera That Were Negative Both for Toxoplasma Antibody and for RF

Each of the 28 serum samples that were negative for Toxoplasma antibody in the DT and IgM-IFA test and negative for RF were negative with NIgG, with TIgG, and with the F(ab')2 fragment of TIgG.

Results in Sera That Were Negative for Toxoplasma Antibody and Positive for RF

Twelve of 13 serum samples that were negative for Toxoplasma antibody in the DT and IgM-IFA test and positive for RF reacted strongly with NIgG and with TIgG but were negative with both of the F(ab')2 fragments. One serum sample (RF titer 1:2560) was negative on initial and repeat testing.

Results in Sera from Individuals Chronically Infected with Toxoplasma

Of 55 sera, two reacted only with NIgG and two reacted both with NIgG and with TIgG. All 55 sera were negative and both of the F(ab')2 fragments. The absence of reactivity with the F(ab')2 fragments was not a matter of concentration of these preparations in the wells since no differences in the results were noted when the concentrations were increased to 10-fold higher than the concentrations of NIgG and TIgG. These results and the following results suggest that the test can distinguish between chronic and acute Toxoplasma infections.

Results in Sera from Individuals with Recently Acquired (Acute) Toxoplasmosis

The results in 23 sera from 22 patients are shown in Table 2. Ten (43.4%) sera reacted with NIgG, with TIgG, and with the F(ab')2 fragment of TIgG. Five (21.7%) sera reacted with TIgG and with the F(ab')2 fragment of TIgG but not with NIgG. One (4.3%) serum sample reacted only with NIgG. None were positive with the F(ab')2 fragment of NIgG. Seven (30.4%) sera were negative with NIgG, with TIgG, and with the F(ab')2 fragment of TIgG, although biopsy of lymph nodes was suggestive of Toxoplasmosis in five of the seven patients from whom these seven sera were obtained.

TABLE 2

| Patient* | Time from onset of clinical illness to serum collected (wks)** | Reactive with | | | Serologic test titers$^{-1}$ | |
|---|---|---|---|---|---|---|
| | | NIgG | TIgG | F(ab')2 fragment of TIgG | DT | IgM-IFA |
| TC | 1 | + | + | + | 16000 | 160 |
| HC | 2 | + | + | + | 512 | 20 |
| AP | 3 | − | + | + | 4096 | 320 |
| CP | 3 | − | − | − | 16000 | 160 |
| FC | 3 | + | + | + | 2048 | 8 |
| JW | 3 | − | + | + | 4096 | 2560 |
| SM# | 3 | − | + | + | 4096 | 64 |
| AB | 4 | − | + | + | 16000 | 80 |
| AS | 4 | + | + | + | 16000 | 160 |
| CB | 4 | + | + | + | 16000 | 1024 |
| HG | 4 | + | + | ±*** | 4096 | 256 |
| LS | 4 | ±*** | + | + | 8000 | 40 |
| SM# | 6 | + | + | + | 8000 | 16 |
| WC | 6 | − | − | − | 8000 | 160 |
| BS | 8 | − | − | − | 32000 | 320 |
| EK | 8 | + | + | + | 4096 | 160 |
| JL | 8 | + | − | − | 32000 | 64 |
| KD | 8 | − | + | + | 64000 | — |
| LB | 8 | − | − | − | 32000 | 160 |
| PD | 8 | − | − | − | 1096 | 640 |
| DC | 12 | − | − | − | 4096 | 40 |
| MH | 20 | + | + | + | 2048 | 16 |
| MW | 20 | − | − | − | 32000 | 640 |

*All patients had lymphadenopathy except patient LB (who had persistent fever) and patient FC (who was infected in a laboratory accident). Patients TC, CP, AS, CB, LS, WC, BS, EK, JL, PD, MH, and MW had characteristic histologic features of Toxoplasmosis on lymph node biopsy.
**The time recorded is an approximation from data in the patient clinical record.
***Weakly positive.
Same patient.

EXAMPLE 2

This example illustrates the use of monoclonal antibodies to antigens of *Toxoplasma gondii* in a sandwich immunoassay for Toxoplasma antigenemia.

Preparation of Monoclonal Antibodies to *Toxoplasma gondii*

The monoclonal antibodies were prepared as follows:

Myeloma Cells

The parental myeloma cell line used was the NS-1 variant of the P3 (MOPC-21) line (Köhler & Milstein, *Nature*, 256:495, 1975).

Immunisation and Fusion with Spleen Cells

BALB/c female mice, 8 weeks of age (Palo Alto Medical Research Foundation colony), were infected subcutaneously with $2 \times 10^3$ Toxoplasma tachyzoites of the relatively avirulent C37 strain. The mice were boosted intraperitoneally 50 days later with $5 \times 10^6$ formalin fixed tachyzoites. Three days later the spleens were removed and the spleen cells suspended in serum free RPMI-1640 (Flow Laboratories, Rockville, Md.). The methods for cell fusion were as described by Köhler and Milstein, supra. In brief, spleen cells $(1.5 \times 10^8)$ were mixed with NS-1 cells $(1.5 \times 10^8)$ and pelleted by centrifugation at 200 g for 10 min. The cells were fused by resuspending the pellet in RPMI-1640 containing 50% (wt/vol) polyethylene glycol (BDH Chemicals, Ltd, Poole, England). The cells were washed, resuspended in RPMI-1640 with 15% fetal bovine serum (Flow Laboratories, Rockville, Md.), and cultured in 96 well microculture plates (Costar, Cambridge, Mass.). Approximately $10^6$ cells were cultured in each well.

Growth of Antibody Producing Cell Hybrid

One day after the fusion, 100 ul of RPMI-1640 with 15% fetal bovine serum and containing hypoxanthine (0.014 g/l), aminopterin (0.176 g/l), and thymidine (0.0039 g/l) (HAT medium) were added to each well. During the second to fourth week, depending on the rate of cell growth, supernatants were tested for antibody activity. Hybrids selected for reactivity to *Toxoplasma gondii* were cultured further in 24 well culture plates (Costar, Cambridge, Mass.) with $5 \times 10^6$ mouse thymocytes as "feeder" cells, and then expanded into larger flasks.

Cloning was performed by limiting dilution in microculture plates using $1 \times 10^6$ mouse thymocytes "feeder" cells per well and three different concentrations of cells; 36 wells containing 5 cells each, 36 wells containing 1 cell each, and 24 wells containing 0.5 cells each were cultured for every selected hybrid. After cloning, cells from cultures expressing the highest antibody production were expanded into larger cultures as described above. For storage, $10^6$ cells were frozen in 0.5 ml fetal bovine serum containing 10% dimethyl sulfoxide and placed in liquid nitrogen or at $-70°$ C. Cells ($2-5 \times 10^6$) from each clone were injected subcutaneously into BALB/c mice and tumors (hybridomas) appeared within 20-30 days. The mice were bled every few days, the sera were pooled and stored at $-70°$ until used.

Antibody Assays of Culture Supernatants

Reactivity against soluble Toxoplasma antigens was measured by a solid phase radioimmunoassay (RIA) using antigen coated polyvinyl chloride plates (Cooke Lab Products, Alexandria, Va.). Soluble Toxoplasma proteins were prepared by hypotonic lysis and sonication of washed tachyzoites. Insoluble material was discarded after centrifugation at 27,000 g for 60 min and the supernatant used as soluble antigens in the RIA. The protein concentration was adjusted to 1 mg/ml and 100 $\mu$l were dispensed into each well of a 96 well plate. The proteins were passively adsorbed to the plastic (60 min at room temperature), the excess washed off, and any remaining non-specific binding sites on the plastic, saturated by washing with 1% BSA (Miles Laboratories, Inc) in PBS, pH 7.4. Antigen coated wells were reacted with 25 mcl of culture supernatant for 60 min at room temperature, washed in RIA buffer, and incubated for an additional 60 min at room temperature with 50 mcl $^{125}$I-labeled protein A (New England Enzyme Center) 40 microCi/mcl; 10,000 cpm per well. The wells were cut and counted in a gamma-counter.

Those supernatants containing anti-Toxoplasma antibodies were passed through a protein A Sepharose column (Pharmacia Fine Chemicals, Uppsala, Sweden) to obtain the IgG fraction. Protein concentration in the fractions was determined by the Lowry method with BSA as standard. Antibody activity against Toxoplasma gondii in the IgG fractions was determined by the DT and IgM-IFA tests.

*Toxoplasma gondii* Antigen

Toxoplasma lysate (TL) was prepared as described in Example 1. The protein concentration of the lysate preparation was 0.52 mg/ml. The lysate was stored, lyophylized and reconstituted with PBS, pH 7.2, before use.

Peritoneal Fluid (PF)

Three milliliters of PBS were injected into the peritoneal cavities of mice which had been infected intraperitoneally with a number of tachyzoites of the RH strain of *Toxoplasma gondii* two days earlier. The fluid was then aspirated and cleared of parasites and cells by centrifugation ($1500 \times g$ for 15 min) and the supernatant was centrifuged again at $10,000 \times g$ for 30 min. The supernatant from the second centrifugation was filtered through a millipore filter (0.45 nm pore size), divided into aliquots and frozen at $-20°$ C. until use.

Serum Samples

The sera used were 37 samples from individuals who did not have serologic evidence of infection with *Toxoplasma gondii* as determined by the DT and IFA test, 14 samples from individuals chronically infected with *Toxoplasma gondii* as determined by serology and by clinical history, four samples from patients acutely infected with *Toxoplasma gondii* in which Toxoplasma antigens were demonstrated previously. Five serum samples from individuals with a positive serology for RF but with negative DT and IFA test titers were employed to determine whether RF positive serum would react with the monoclonal antibody used to coat the wells. In addition, ten serum samples from patients who had positive serology for antinuclear antibodies (titers 1:40 to 1:640) as demonstrated by the fluorescent antinuclear antibody test (FANA) were also examined as a possible source of false-positive results. These latter sera were also negative in the IFA and DT tests.

Performance of Sandwich Immunoassay for *Toxoplasma gondii* Antigen

The procedure employed was that of Example 1. Table 3 gives the results of assays using six monoclonal antibodies prepared as above and Toxoplasma lysate (TL) prepared as in Example 1. The protein concentration of all monoclonal antibodies was adjusted to 0.8 mg/ml. A control test using the F(ab')$_2$ fragment of a rabbit anti-Toxoplasma IgG was performed in parallel. In the test an optical density reading of 0.02 was compatible with negative results. Any OD readings three or more times higher than the average reading of the negative controls was considered positive. Two of the monoclonal antibodies (identified as 3B4 and 3G3) did not detect Toxoplasma antigens either in the TL or in the PF and four (identified as 5B6, 1E11, 2G11 and 3E6) detected antigens in both preparations. The two that did not detect antigens were found by radioimmunoassay to be directed against cytoplasmic antigens only. The four that did detect antigens were found by a similar test to be directed against membrane antigens or both membrane and cytoplasmic antigens.

TABLE 3

| Monoclonal Antibody | OD | |
| --- | --- | --- |
| | PF | TL |
| 3B4 | 0.02 | 0.02 |
| 3G3 | 0.02 | 0.02 |
| 5B6 | 0.09 | 0.15 |
| 1E11 | 0.79 | 0.26 |
| 2G11 | 0.21 | 0.26 |
| 3E6 | 0.35 | 0.23 |
| Control | 0.47 | 0.29 |

To determine the lowest amount of Toxoplasma antigen in the TL preparation which could be detected by the monoclonal antibodies, wells of microtiter plates were coated with either 1E11, 2G11 or 3E6 at a concentration of 40 μg protein/ml and tested with various concentrations of the TL preparation. The differences in the OD readings obtained with concentrations of monoclonal antibody of 20, 40, and 80 mcg/ml were very small. The results were similar for all three monoclonal antibodies. A concentration of 40 mcg/ml was determined to be optimal for coating the wells.

To show that the monoclonal antibodies may be useful to detect Toxoplasma antigens in serum of patients with acute acquired Toxoplasmosis, individual wells of microtiter plates were coated with 2G11, 1E11 and 3E6 at a concentration of 40 mcg protein/ml. 5B6 was used at a concentration of 0.8 mg/ml. As a positive control the F(ab')2 fragment of Example 1 was used at a concentration of 20 mcg protein/ml. Each of the four monoclonal antibodies detected *Toxoplasma gondii* antigens in the sera of patients with acute Toxoplasmosis. All serum samples of individuals not infected with *Toxoplasma gondii*, of individuals chronically infected with the parasite, and of individuals with a positive RF titer had OD readings which were no greater than negative control sera. Of the ten FANA positive sera, two (FANA titers 1:320 and 1:640) reacted (OD=0.29 and 0.11). Other FANA positive sera with similar FANA titers did not react in the sandwich immunoassay. The conjugate (enzyme labeled antiToxoplasma IgG) and the substrate did not react with the monoclonal antibodies coating the wells.

Modifications of the above described aspects of the invention that are apparent to those of skill in the fields of medicine, and in particular immunology, are intended to be within the scope of the following claims.

We claim:

1. An immunoassay for detecting *Toxoplasma gondii* antigen associated with an acute form of Toxoplasma infection in a sample of an animal body fluid comprosing the steps of:
   (a) adsorbing an F(ab')2 fragment of IgG *Toxoplasma gondii* antibody or a monoclonal antibody for antigens of *Toxoplasma gondii* onto a solid surface;
   (b) adding the sample to the adsorbed fragment of step (a) and incubating the resulting mixture;
   (c) separating the adsorbed fraction from the nonadsorbed fraction of the incubated mixture of step (b);
   (d) adding a labeled *Toxoplasma gondii* antibody to the adsorbed fraction of step (c) and incubating the resulting mixture;
   (e) separating the adsorbed fraction from the nonadsorbed fraction of the incubated mixture of step (d); and
   (f) determining the presence of labeled *Toxoplasma gondii* antibody in the adsorbed fraction of step (e).

2. The immunoassay of claim 1 wherein in step (a) the F(ab')2 fragment is in the form of an F(ab')2 fragment preparation having a protein concentration of 20 to 40 mcg/ml.

3. The immunoassay of claim 1 wherein the monoclonal antibody is a monoclonal IgG antibody for membrane antigens of *Toxoplasma gondii*.

4. The immunoassay of claim 3 wherein the monoclonal antibody is in the form of a preparation having a monoclonal antibody concentration of about 40 mcg/ml.

5. The immunoassay of claim 1 wherein the label of the labeled antibody is an enzyme label.

6. The immunoassay of claim 1 wherein the labeled antibody of step (d) is a whole IgG.

* * * * *